United States Patent [19]

Lang et al.

[11] Patent Number: 5,403,841
[45] Date of Patent: Apr. 4, 1995

[54] USE OF CARRAGEENANS IN TOPICAL OPHTHALMIC COMPOSITIONS

[75] Inventors: John C. Lang, Arlington; Jamieson C. Keister, Crowley; Paul J. T. Missel, Arlington, all of Tex.; Dimitri J. Stancioff, Camden, Me.

[73] Assignee: Alcon Laboratories, Inc., Forth Worth, Tex.

[21] Appl. No.: 108,824

[22] Filed: Aug. 18, 1993

Related U.S. Application Data

[63] Continuation of Ser. No. 924,384, Aug. 3, 1992, abandoned, which is a continuation of Ser. No. 641,214, Jan. 15, 1991, abandoned.

[51] Int. Cl.$^6$ ............... A61K 31/54; A61K 31/415; A61K 31/715
[52] U.S. Cl. ............... 514/226.8; 514/54; 514/392; 514/912
[58] Field of Search ............ 514/392, 54, 226.8, 514/912

[56] References Cited

U.S. PATENT DOCUMENTS

| | | | |
|---|---|---|---|
| 4,014,335 | 3/1977 | Arnold | 424/21 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,565,821 | 1/1986 | Chiou | 514/329 |
| 4,638,059 | 1/1987 | Sutherland | 536/121 |
| 4,708,861 | 11/1987 | Popescu et al | 424/1.1 |
| 4,861,760 | 8/1989 | Mazuel et al. | 514/54 |

OTHER PUBLICATIONS

Glicksman, M., *Gum Technology in the Food Industry*, New York: Academic Press, 1969, pp. 218–219.
Harris, P. (ed.), *Food Gels*, New York: Elsevier Applied Science, 1990, Ch. 3 (pp. 79–119) and Ch. 6 (pp. 201–232).
Hawley, G., *The Condensed Chemical Dictionary*, 10th ed., Van Nostrand Reinhold Co., 1981, p. 202.
Stancioff, D., "Reflections in the Interrelationships Beteen Red Seaweed Source chemistry and Uses," *Xth Int. Seaweed Symp.* (ed. T. Levring), New York: Walter de Gruyter & Co., 1981, pp. 113–212.
Stancioff, D. et al., "Infrared and Chemical Studies on Algal Polysaccharides," *Proc. VIth Int. Seaweed Symp.* (ed. R. Margalef), sy Madrid: Subsecretaria de la Marina Mercante, 1969, pp. 595–609.

*Primary Examiner*—Zohreh Fay
*Attorney, Agent, or Firm*—Julie J. L. Cheng

[57] ABSTRACT

Topical ophthalmic compositions of carrageenans which are administrable as a drop but which become more viscous or gel upon instillation in the eye are disclosed. Methods for use of the compositions as topical ophthalmic vehicles for pharmaceutically active agents, and alone as lubricants or tear supplements, are also disclosed.

13 Claims, No Drawings

USE OF CARRAGEENANS IN TOPICAL OPHTHALMIC COMPOSITIONS

This application is a continuation of application Ser. No. 07/924,384, filed on Aug. 3, 1992, which is a continuation of application Ser. No. 07/641,214, filed Jan. 15, 1991, both now abandoned.

BACKGROUND OF THE INVENTION

1. Field of the Invention

The present invention relates to the use of adjuvants in topical ophthalmic compositions. In particular, this invention relates to the use of carrageenans and furcellarans in the compositions and a method for the controlled administration of a pharmaceutically active agent to patients wherein the topical compositions are administered as partially gelled liquids which thicken to form gels upon instillation into the eye. The transition from liquid to gel is primarily due to the change in ionic strength, especially an increase in the sodium chloride concentration.

2. Description of Related Art

Topical ophthalmic compositions have taken the form of liquids, ointments, gels and inserts. Liquid compositions for drop-wise instillation of pharmaceutically acceptable agents to the eye provide for easy formulation, but they do not always provide for an accurate dosage amount, as portions of the liquid are often blinked away during administration or drained down the punctum into the nasal passage. Ointments and gels, which usually reside in the eye longer than a liquid and therefore provide for more accurate administration, often interfere with a patient's vision. Ocular inserts, both bioerodible and nonbioerodible, are also available and allow for less frequent administration of drug; however, these inserts require complex and detailed preparation and are frequently uncomfortable to the wearer. An additional problem with the non-bioerodible inserts is that they must be removed after use.

U.S. Pat. Nos. 4,136,173 (Pramoda, et al.); 4,136,177 (Lin, et al.) and 4,136,178 (Lin, et al.) disclose the use of therapeutic compositions containing xanthan gum and locust bean gum which are delivered in liquid form and which gel upon instillation. In these three patents, the mechanism for transition from liquid to gel is due to a change in pH.

U.S. Pat. No. 4,861,760 (Mazuel, et al.) discloses ophthalmological compositions containing gellan gum which are administered to the eye as non-gelled liquids and which gel upon instillation due to the change in ionic strength.

SUMMARY OF THE INVENTION

The present invention is directed to topical ophthalmic compositions comprising carrageenans and furcellarans (hereinafter "carrageenans") which provide for controlled administration of a drug to the eye and methods for their use. It is noted here that furcellarans are generally considered carrageenans except in the U.S. for regulatory purposes. In addition, the compositions can be administered without containing a pharmaceutically active agent to lubricate the eye or to supplement tears in the treatment of, for example, dry eye. The compositions are administered as liquids or partially gelled liquids (hereinafter "liquids") which thicken to form gels upon instillation into the eye. The carrageenans are sulfated polysaccharides extracted from red seaweeds and are of the type which, when formulated in the compositions of the present invention, undergo gelation when exposed to a salinity level characteristic of that present in tears.

DETAILED DESCRIPTION OF THE INVENTION

Carrageenans are widely used as thickeners, viscosity modifiers, and as thixotropic and gelling agents. Although they may be characterized as gelling and non-gelling, for purposes of the present invention, only the carrageenans capable of forming reversible gels are of interest. The carrageenans suitable for use in this invention may be generally characterized as capable of gelling in 0.5 to 1.0% aqueous NaCl solution (representative of human tears). Of the many known gelling carrageenans, those extracted from the algal species *Eucheuma gelatinae*, *Eucheuma speciosum*, *Endocladia muricata*, *Furcellaria fastigata* (i.e., furcellaran) and kappa carrageenan from *Eucheuma cottonii* and closely related species of *Rhodophyceae* (red seaweeds), such as Hypnea, give the best results for the purposes of the present invention.

Carrageenans are polysaccharides which are straight chain galactan sulfates of high molecular weight with a backbone composed essentially of alternating copolymers of $\beta$-(1->3)-D-galactose and $\beta$-(1->4)-3,6-anhydro D- or L-galactose. In kappa-carrageenan, nearly every D-galactose is sulfated at position 4. In furcellaran, *Eucheuma gelatinae*, *Eucheuma Speciosum* and *Endocladia muricata* carrageenans, about half of the D-galactose is sulfated at position 4 and the other half is not. Thus, in kappa carrageenan there is about one sulfate per disaccharide repeating unit and in the furcellaran and *Eucheuma gelatinae* carrageenans there is an average of about one sulfate for every two disaccharide repeating units. The furcellarans and carrageenans referred to herein were extracted and purified by and are obtainable from FMC Corporation, Marine Colloids Division (Philadelphia, Pa.).

Particularly preferred carrageenans for the purposes of the present invention are those extracted from *Eucheuma gelatinae* and *Furcellaria fastigiata*, which have the lowest degree of sulfation, and carrageenans obtained from *Eucheuma speciosum* and *Endocladia muricata*. These provide for the greatest contrast in the ratio of gel elastic modulus to viscosity, as explained below. As is known in the art, a preferred procedure for obtaining these carrageenans is by alkaline extraction at a pH of between 10 and 14 in order to obtain maximum gelling properties.

The compositions of the present invention may be formulated in many ways, for example: 1) a "liquid formulation," wherein the composition is a low viscosity liquid which becomes a high viscosity liquid or a gel upon instillation in the eye; 2) a "stiff gel formulation," wherein the composition is a weak gel which becomes a stiffer gel in the eye; and 3) a "thixotropic formulation," wherein the composition is a viscous liquid when shaken but is a fractured gel when left standing for a period of time. Upon instillation, the formulation becomes a stiff gel. Carrageenans are typically present in these formulations at a concentration in the range of about 0.1% to about 3.0%. It is preferred that the carrageenans in these formulations are present in the form of their sodium salts. Actual carrageenan concentration will vary, to provide for formulations with viscosity and modulus of elasticity ranges as described below.

The different types of formulations discussed above exhibit different physical characteristics. For the sake of clarity and for ease of reference in the following discussion, "pre-dosed" refers to formulations before their administration to the eye and "post-dosed" refers to formulations after their administration.

The liquid compositions of the present invention comprise a carrageenan to provide formulations having pre-dosed viscosity in the range of about 1 to about 500 centipoise (cps), with about 1 to about 200 cps preferred, and about 1 to about 100 cps most preferred. If it is desirable that the liquid formulations do not form a gel upon administration to the eye, but simply become more viscous, the compositions should be formulated to provide a post-dosed viscosity which will be greater than about 50 cps, preferably greater than about 150 cps, and most preferably greater than about 300 cps. If it is desirable that the liquid formulations form a gel in the eye, the compositions should be formulated to provide for a post-dosed modulus of elasticity (Young's modulus) in the range of about $1 \times 10^4$ to about $5 \times 10^5$ dynes/cm$^2$, with about $2 \times 10^4$ to about $5 \times 10^5$ dynes/cm$^2$ preferred and about $5 \times 10^4$ to about $5 \times 10^5$ dynes/cm$^2$ most preferred.

The stiff gel formulations comprise a carrageenan to provide for a composition with a pre-dosed modulus of elasticity in the range of about $1 \times 10^4$ to about $3 \times 10^5$ dynes/cm$^2$, with about $2 \times 10^4$ to about $2 \times 10^5$ dynes/cm$^2$ preferred and about $5 \times 10^4$ to about $1 \times 10^5$ dynes/cm$^2$ most preferred. The post-dosed stiff gel formulation is a gel having a modulus of elasticity in the range of about $1 \times 10^4$ to about $2 \times 10^6$ dynes/cm$^2$, with $1 \times 10^5$ to about $7 \times 10^5$ dynes/cm$^2$ preferred and about $2 \times 10^5$ to about $5 \times 10^5$ dynes/cm$^2$ most preferred.

The thixotropic formulations contain carrageenan so that, when shaken, the composition will have a pre-dosed viscosity in the range of about 1 to about 5000 cps, with about 50 to about 1000 cps preferred and about 200 to about 500 cps most preferred. The unshaken thixotropic formulation will be in the form of a fractured gel or a gel with pre-dosed modulus of elasticity in the range of about $1 \times 10^4$ to about $2 \times 10^5$ dynes/cm$^2$, with about $2 \times 10^4$ to about $1 \times 10^5$ dynes/cm$^2$ preferred and about $3 \times 10^4$ to about $7 \times 10^4$ dynes/cm$^2$ most preferred. The post-dosed gel will have a modulus of elasticity in the range of about $1 \times 10^4$ to about $2 \times 10^6$ dynes/cm$^2$, with about $2 \times 10^4$ to about $1 \times 10^5$ dynes/cm$^2$ preferred and about $3 \times 10^4$ to about $7 \times 10^4$ dynes/cm$^2$ most preferred.

Although the carrageenan liquid-to-gel transition is primarily initiated by an increase in ionic strength, such factors as a change in temperature, or characteristics and concentrations of drugs or other adjuvants may also affect the liquid-to-gel transition. In addition, the strength of the carrageenan gels of the present invention may be influenced by the presence of alkali metal ions or polymers, such as polysaccharides and polyols.

Pharmaceutically active agents ("drugs") which can be included in the compositions of the present invention and administered via the method of the present invention include, but are not limited to: glaucoma agents, such as betaxolol, pilocarpine and carbonic anhydrase inhibitors; dopaminergic agonists; post-surgical antihypertensive agents, such as para-amino clonidine (apraclonidine); anti-infectives, such as ciprofloxacin; non-steroidal and steroidal anti-inflammatories, such as suprofen, ketorolac and tetrahydrocortisol; prostaglandins; proteins; growth factors, such as epidermal growth factor; and anti-allergics. In a formulation without the use of drugs, the present invention may also serve to supplement tears in the prevention or treatment of dry eye.

The compositions of the present invention can include other components, for example, ophthalmically acceptable buffers, preservatives, and tonicity agents.

In general, the compositions of the present invention are formulated such that the carrageenan is added last, after all the other ingredients have been mixed. Where the drugs to be included in the compositions of the present invention have a low solubility, it is preferred that the ophthalmic agent be added last, that is, after the addition of the carrageenan. In certain cases, it may also be preferred that the drug be separately sterilized (e.g., with radiation) and aseptically added to the other ingredients, which have been autoclaved according to the sterilization procedure described below.

Sterilization of the compositions can be accomplished by autoclaving. It is well known that an order of magnitude reduction in sterilization time is achieved for every 10° C. rise in sterilization temperature. As the carrageenans tend to decompose and undergo a non-enzymatic browning reaction (i.e., caramelize) when heated, sterilization at higher temperatures with lower sterilization time is generally preferred. The preferred temperature range is greater than about 130° C., with a sterilization time of less than about 3 minutes when the pH of the composition is more than about 6. In those instances where the final pH of the composition is less than 6, it is preferred that sterilization take place at pH close to 7.4, then to adjust the pH by aseptic means to its final value.

The following examples are presented to illustrate further various aspects of the present invention, but are not intended to limit the scope of the invention in any respect.

EXAMPLE 1

The following are examples of stiff gel formulations:

| INGREDIENTS | Percent by weight/volume | | | | | | | | |
|---|---|---|---|---|---|---|---|---|---|
| | A | B | C | D | E | F | G | H | I |
| Eucheuma Carrageenani[1] | 2.0 | — | 1.2 | 1.2 | 1.2 | 1.2 | 1.2 | 1.2 | 1.2 |
| Furcellaran[2] | — | 2.0 | — | — | — | — | — | — | — |
| Na$_2$HPO$_4$ | 0.1 | 0.1 | — | — | 0.1 | 0.1 | 0.1 | 0.1 | — |
| Maleic Acid | — | — | 0.12 | 0.12 | — | — | — | — | 0.12 |
| Tromethamine | — | — | 0.24 | 0.24 | — | — | — | — | 0.22 |
| Mannitol | 3.9 | 3.9 | 4.2 | 4.0 | 3.0 | 3.5 | 3.5 | 4.0 | 3.6 |
| Apraclonidine | — | — | — | 0.25 | — | — | — | — | — |
| Pilocarpine | — | — | — | — | 1.0 | — | — | — | — |
| S-Betaxolol (free base) | — | — | — | — | — | — | — | 0.5 | — |
| Suprofen | — | — | — | — | — | 1.0 | — | — | — |
| Timolol | — | — | — | — | — | — | 1.0 | — | — |
| AL04414A[3] | — | — | — | — | — | — | — | — | 1.0 |

[1]Extract from *Eucheuma gelatinae*.
[2]Extract from *Furcellaria fastigiata*.
[3](+)-4-Ethylamino-2,3-dihydro-4H-2-methylthieno[3,2-e]-1,2-thiazine-6-sulfonamide-1,1-dioxide HCl.

The compounding procedure for Formulation A is detailed below. Analogous procedures are utilized to prepare other formulations.

Preparation of Formulation A

The following procedure was utilized to prepare a 50 milliliter (ml) batch of Formulation A.

Approximately 30 ml of water (about 2/3 of the final volume), 0.050 grams (g) of Na$_2$HPO$_4$ (0.1% w/v) and 2.498 g of mannitol (5% w/v) were added to a beaker equipped with a magnetic stir bar. The mixture was stirred until the ingredients were dissolved. The pH of the mixture was lowered from 8.64 to 7.43 by the addition of 0.1N HCl. Water was added to bring the final volume to 50 ml. The mixture was then heated to 90° C. When the temperature of the mixture reached 90° C., 1.002 g of eucheuma carrageenan (2%) was added. The mixture was stirred for ½ hour while the temperature was maintained at 90° C. When the mixture was removed from the heat, the osmolality was checked. The final osmolality was 355 milliOsmolal (mOsm).

The mixture was sterilized in an autoclave at 130° C. for 3 minutes in containers having radii no greater than 1 centimeter (cm). After sterilization, the containers were removed and allowed to air cool to room temperature.

EXAMPLE 2

The following are examples of thixotropic formulations:

| Ingredient | Percent by weight/volume | | |
|---|---|---|---|
| | A | B | C |
| Eucheuma Carrageenan | 0.6 | 0.6 | 0.8 |
| Na$_2$HPO$_4$ | 0.1 | 0.1 | 0.1 |
| Mannitol | 3.5 | 3.5 | 4.2 |
| Hydroxyethoxzolamide | — | 1–3 | 1–3 |
| Apraclonidine | — | — | ≦1 |

Compounding procedures for these formulations are similar to the procedure detailed in Example 1, above.

EXAMPLE 3

The following are examples of liquid formulations:

| Ingredient | Percent by weight/volume | | | | | | |
|---|---|---|---|---|---|---|---|
| | A | B | C | D | E | F | G |
| Eucheuma Carrageenan | 0.3 | — | — | 0.5 | 0.5 | 1.2 | 1.2 |
| Kappa Carrageenan[1] | — | 0.5 | — | — | — | — | — |
| Furcellaran | — | — | 0.3 | — | — | — | — |
| Na$_2$HPO$_4$ | 0.1 | 0.1 | 0.1 | 0.1 | 0.1 | 0.1 | 0.1 |
| Mannitol | 3.5 | 3.5 | 3.5 | 3.5 | 3.5 | 3.2 | 3.2 |
| S-Betaxolol (free base) | — | — | — | 0.5 | — | — | — |
| Pilocarpine | — | — | — | — | 1.0 | — | — |
| MK 927[2] | — | — | — | — | — | — | 2.0 |
| AL04414A | — | — | — | — | — | 2.0 | — |

[1] Extract from *Eucheuma cottonii*.
[2] 5,6-Dihydro-4-isobutylamino-4H-thieno[2,3-b]thiopyran-2-sulfonamide-7,7-dioxide HCl.

Compounding procedures are similar to the procedure detailed in Example 1, above.

The invention in its broader aspects is not limited to the specific details shown and described above. Departures may be made from such details within the scope of the accompanying claims without departing from the principals of the invention and without sacrificing its advantages.

What is claimed is:

1. A method of delivering a drug to the eye which comprises topically administering a composition comprising a drug and a carrageenan capable of gelation upon exposure to sodium ions at concentrations found in lachrymal fluid, wherein the carrageenan is present at a concentration which allows the composition to be administrable as a drop which gels upon instillation to the eye, wherein the carrageenan has not more than about 1.0 sulfate moieties per disaccharide repeating unit.

2. The method of claim 1 wherein the carrageenan concentration is between about 0.1% to about 3.0% by weight/volume.

3. The method of claim 1 wherein the carrageenan has an average of less than about 0.5 sulfate moieties per disaccharide repeating unit.

4. The method of claim 1 wherein said carrageenan is extracted from *Eucheuma gelatinae*.

5. The method of claim 1 wherein said carrageenan is extracted from *Furcellaria fastigiata*.

6. The method of claim 1 wherein the drug is para-amino clonidine.

7. The method of claim 1 wherein the drug is a carbonic anhydrase inhibitor.

8. The method of claim 7 wherein the carbonic anhydrase inhibitor is (+)-4-ethylamino-2,3-dihydro-4H-2-methylthieno[3,2-e ]-1,2-thiazine-6-sulfonamide-1,1-dioxide or a pharmaceutically acceptable salt thereof.

9. The method of claim 1, wherein said carrageenan is extracted from an algae selected from the group consisting of: *Eucheuma gelatinae, Eucheuma speciosum, Endocladia muricata, Furcellaria fastigiata* and *Eucheuma cottonii*.

10. The method of claim 1 wherein the pre-dosed viscosity is in the range of about 1 to about 500 cps and the post-dosed viscosity is greater than about 50 cps.

11. The method of claim 1 wherein the pre-dosed viscosity is in the range of about 1 to about 500 cps and the post-dosed gel has a modulus of elasticity in the range of $1 \times 10^4$ to about $5 \times 10^5$ dynes/cm$^3$.

12. The method of claim 1 wherein the pre-dosed modulus of elasticity is in the range of about $1 \times 10^4$ to about $3 \times 10^5$ dynes/cm$^2$ and the post-dosed modulus of elasticity is in the range of about $1 \times 10^4$ to about $2 \times 10^6$ dynes/cm$^2$.

13. The method of claim 1 wherein the composition is thixotropic, having a pre-dosed modulus of elasticity in the range of about $1 \times 10^4$ to about $2 \times 10^5$ dynes/cm$^2$ and, when shaken, a pre-dosed viscosity in the range of about 1 to about 5000 cps and having a post-dosed modulus of elasticity in the range of about $1 \times 10^4$ to about $2 \times 10^6$ dynes/cm$^2$.

* * * * *